(12) United States Patent
Richardson et al.

(10) Patent No.: US 9,168,251 B2
(45) Date of Patent: Oct. 27, 2015

(54) HIGH DOSE BUPRENORPHINE COMPOSITIONS AND USE AS ANALGESIC

(75) Inventors: Rachel A. Richardson, Grayslake, IL (US); Carmela H. Luangdilok, Westmont, IL (US); Luk Chiu Li, Lake Forest, IL (US)

(73) Assignee: Zoetis Belgium S.A, Louvain-La-Neuve (BE)

( * ) Notice: Subject to any disclaimer, the term of this patent is extended or adjusted under 35 U.S.C. 154(b) by 9 days.

(21) Appl. No.: 13/818,013

(22) PCT Filed: Sep. 2, 2011

(86) PCT No.: PCT/US2011/050413
§ 371 (c)(1),
(2), (4) Date: Sep. 25, 2013

(87) PCT Pub. No.: WO2012/031252
PCT Pub. Date: Mar. 8, 2012

(65) Prior Publication Data
US 2014/0329843 A1     Nov. 6, 2014

Related U.S. Application Data

(60) Provisional application No. 61/379,996, filed on Sep. 3, 2010.

(51) Int. Cl.
| | | |
|---|---|---|
| A61K 31/44 | (2006.01) | |
| A01N 43/42 | (2006.01) | |
| A61K 31/485 | (2006.01) | |
| A61K 9/00 | (2006.01) | |
| A61K 47/14 | (2006.01) | |

(52) U.S. Cl.
CPC ............ *A61K 31/485* (2013.01); *A61K 9/0019* (2013.01); *A61K 47/14* (2013.01)

(58) Field of Classification Search
CPC .... A61K 31/485; A61K 47/14; A61K 9/0019
USPC .................................................. 514/279, 280
See application file for complete search history.

(56) References Cited

U.S. PATENT DOCUMENTS

| | | | | |
|---|---|---|---|---|
| 5,240,711 | A * | 8/1993 | Hille et al. ..................... | 424/448 |
| 5,968,547 | A * | 10/1999 | Reder et al. .................... | 424/449 |
| 2007/0116730 | A1* | 5/2007 | Simmons et al. ............. | 424/400 |
| 2009/0181068 | A1 | 7/2009 | Dunn | |

FOREIGN PATENT DOCUMENTS

| | | | |
|---|---|---|---|
| WO | 9912606 A1 | 3/1999 | |
| WO | WO 03061632 A1 * | 7/2003 | ............... A61K 9/48 |
| WO | 2005011578 A2 | 2/2005 | |
| WO | 2010009451 A2 | 1/2010 | |

OTHER PUBLICATIONS

Gassel et al., "Comparison of oral and subcutaneous administration of buprenorphine and meloxicam for preemptive analgesia in cats undergoing ovariohysterectomy", 2005, JAVMA (ISSN: 0003-1488), vol. 227, No. 12, pp. 1937-1944.*
Office Action mailed Mar. 12, 2014 for European Application No. EP11758027 filed Sep. 2, 2011.
Budd K., "High Dose Buprenorphine for Postoperative Analgesia," Anaesthesia, 1981, vol. 36 (9), pp. 900-903.
Compton P., et al., "Pharmacokinetics, Bioavailability and Opioid Effects of Liquid Versus Tablet Buprenorphine," Drug and Alcohol Dependence, 2006, vol. 82 (1), pp. 25-31.
International Search Report and Written Opinion for Application No. PCT/US2011/050413, mailed on Dec. 5, 2011, 9 pages.
Patent Examination Report mailed Nov. 11, 2013 for Australian Application No. 2011295694 filed Sep. 2, 2011.

* cited by examiner

*Primary Examiner* — My-Chau T Tran
(74) *Attorney, Agent, or Firm* — Paul M. Misiak; Barbara L. Renda

(57) ABSTRACT

The present disclosure relates to a method of providing prolonged analgesia to a mammal in need thereof. Specifically, the current disclosure is directed to a method of treating pain in a mammal for a prolonged period of time using a single high dose of a buprenorphine formulation.

16 Claims, 9 Drawing Sheets

HIGH DOSE BUPRENORPHINE COMPOSITIONS AND USE AS ANALGESIC

CROSS-REFERENCE TO RELATED APPLICATIONS

This is the U.S. national stage entry of International Patent Application No. PCT/US2011/050413, filed on Sep. 2, 2011, which claims priority to U.S. Provisional Patent Application No. 61/379,996, filed on Sep. 3, 2010, the contents of which are fully incorporated herein by reference.

TECHNICAL FIELD

The present disclosure relates to pharmaceutical compositions and methods of providing analgesia to a mammal in need thereof. Specifically, the current disclosure is directed to pharmaceutical compositions and methods of treating pain in a mammal using a high dose of buprenorphine.

BACKGROUND

Buprenorphine is a semi-synthetic thebaine derivative which acts as a partial µ-opioid receptor agonist and κ-opioid receptor antagonist—an opioid. Opioid receptors are found principally in the central nervous system and the gastrointestinal tract. As a result of the partial agonist activity of buprenorphine at µ-opioid receptors, buprenorphine has a powerful analgesic effect—approximately twenty to forty times more potent as morphine.

Buprenorphine is available in various dosage forms, including sublingual and other oral formulations as well as parenteral dosage forms. The treatment of certain mammals, such as cats and dogs, with a sublingual medication that relies on continuous exposure to the oral mucosa of the mammal's mouth can be difficult to administer, resulting in poor pain control for the mammal. In addition, parenteral dosage forms may be given to mammals by several different routes of administration. Specifically, buprenorphine may be administered intravenously ("IV") and intramuscularly ("IM"). The dosage varies depending on the route of administration. For example, when administered IV, the buprenorphine dose generally ranges from approximately 0.01-0.02 mg/kg of mammal body weight. See U. Krotscheck, D. V. M, D M Boothe D. V. M., and A A Little, D. V. M, Pharmacokinetics of buprenorphine following intravenous administration in dogs, AJVR, Vol. 69, No. 6, June 2008. Similarly, the dosing of buprenorphine for IM administration also ranges from approximately 0.01-0.02 mg/kg of mammal body weight. See L S Slingby, P M Taylor, and A E Waterman-Pearson, *Effects of two doses of buprenorphine four or six hours apart on nociceptive thresholds, pain and sedation in dogs after castration*, THE VETERINARY RECORD, Nov. 18, 2006, pp. 705-711; and S Dobbins, N O Brown, F S Shofer, *Comparison of the Effects of Burprenorphine, Oxymorphone Hydrochloride, and Ketoprofen for Postoperative Analgesia After Onychectomy or Onychectomy and Sterilization in Cats*; JOURNAL OF THE AMERICAN ANIMAL HOSPITAL ASSOCIATION; Vol. 38, November/December 2002, pp. 507-514. Subcutaneous ("SQ") administration of buprenorphine has also been disclosed at doses up to approximately 0.02 mg/kg of mammal body weight. See P V Steagall et al., *Effects of subcutaneous methadone, morphine, buprenorphine or saline on thermal and pressure thresholds in cats*; JOURNAL OF VETERINARY PHARMACOLOGY AND THERAPEUTICS, 2006, Vol. 29, pp. 531-537.

Regardless of the route of administration, all forms of administration of buprenorphine are known to require dosing of the mammal every 2-8 hours for adequate pain control, depending on the route of administration and the pain threshold of the mammal. However, continuous administration of buprenorphine to the mammal by injection can be difficult to perform and stressful to the mammal, further complicating the pain control process. Companion animals, in particular, can be difficult to medicate, so analgesics that provide 24 hours of effect after a single dose would be advantageous. According to CVM-FDA policy, new veterinary pain medications are required to provide 72 hours of post-operative analgesia. Currently, no veterinary product is approved by CVM-FDA that will provide 24 hours of analgesia following a single injection, and can be administered for three consecutive days.

Additionally, the use of higher doses of buprenorphine would be expected to result in adverse effects to the mammal. Specifically, adverse effects associated with high dose buprenorphine include excessive sedation, respiratory depression, excessive salivation, and nausea. Due to the seriousness of such effects, commercially available buprenorphine products, such as the Vetergesic® buprenorphine injection, warns that dosing should not exceed to 10-20 micrograms per kg (0.01-0.02 mg/kg) for analgesia in dogs and cats, repeated if necessary after 2-6 hours.

Extended-release buprenorphine formulations have been developed to prolong the duration of pain control in a mammal. Injectable extended-release formulations, for example, include injectable microparticles, polymer matrix systems, fat emulsions, microspheres, and oil in water emulsions. However, the manufacturing of such formulations is complex and costly, and typically incorporates the use of organic solvents which could introduce potential toxicity if not completely removed. Additionally, it can be difficult to achieve sterility of microparticles and other oil solutions because terminal sterilization is not always possible. It is also difficult to appropriately control the release of a drug such as buprenorphine in an injectable dosage form in order to achieve the desired onset and duration of analgesic effects in the target species. Therefore, it would be desirable to have compositions and less complex methods of providing prolonged pain control to a mammal while minimizing the number of administrations/doses that must be given to the mammal.

SUMMARY

The present disclosure is directed to compositions and methods which include a single high dose non-extended release buprenorphine formulation administered in mammals for prolonged periods of pain control for at least 24 hours without the adverse effects generally expected from high dose treatment.

In embodiments, a method of producing a prolonged analgesic effect in a mammal is provided. The method comprises parenteral administration to a mammal in need thereof of single high dose non-extended release buprenorphine formulation wherein said dose provides adequate analgesia to the mammal for at least twelve hours.

In embodiments, a pharmaceutical composition producing a prolonged analgesic effect in a mammal is provided. The composition comprises a high of buprenorphine wherein said dose provides adequate analgesia to the mammal for at least twelve hours.

The mammals may be companion animals. The companion animals may be canines and felines. In embodiments, the companion animal is feline.

The route of parenteral administration may include subcutaneous, intramuscular, intravenous, intraarterial, intracerebral, intradermal, intrathecal, and intracerebral.

The high dose of buprenorphine may range from about 0.04 mg/kg to about 2 mg/kg of total mammal body weight, from about 0.05 mg/kg to about 1.5 mg/kg of total mammal weight, from about 0.1 mg/kg to about 0.5 mg/kg of total mammal body weight, and from about 0.12 mg/kg to about 0.3 mg/kg of total body weight. In embodiments, the high dose of buprenorphine is about 0.12 mg of buprenorphine per kg of total mammal body weight. In embodiments, the high dose of buprenorphine is about 0.24 mg of buprenorphine per kg of total mammal body weight.

The single high dose non-extended release buprenorphine formulation may provide analgesia to the mammal for a period ranging from about 12 hours to about 48 hours, from about 18 hours to about 30 hours, or for about 24 hours. The single high dose non-extended release buprenorphine formulation may be administered twice per day, once per day, every other day, every two days, or every 48 hours.

The pharmaceutical composition may comprise or consist essentially of a high dose of buprenorphine (such as from about 0.04 mg/kg to about 2.0 mg/kg total mammal body weight). The pharmaceutical composition may be a non-extended release formulation. In embodiments, the pharmaceutical composition is a non-extended release formulation comprising or consisting essentially of buprenorphine in the amount of about 0.12 mg/kg of total mammal body weight. In embodiments, the pharmaceutical composition is a non-extended release formulation comprising or consisting essentially of buprenorphine in the amount of about 0.24 mg/kg of total mammal body weight. The pharmaceutical composition may include a tonicity-adjusting agent and/or at least one antimicrobial agent. In embodiments, the pharmaceutical composition may comprise from about 5% to about 20% of a co-solvent such as ethanol. The pharmaceutical composition may include a tonicity-adjusting agent, at least one antimicrobial agent and/or a co-solvent such as ethanol.

The pharmaceutical composition may comprise or consist essentially of buprenorphine concentrations such as from about 0.5 mg/mL to about 3 mg/mL administered to provide a single high dose of buprenorphine (such as from about 0.12 mg/kg to about 0.24 mg/kg total mammal body weight). The pharmaceutical composition may be a non-extended release formulation. In embodiments, the pharmaceutical composition can also comprise about 3% to about 5% (w/w) of a tonicity-adjusting agent. In embodiments, the pharmaceutical composition may comprise from about 0.05 to about 2.5 mg/mL of at least one antimicrobial agent. In embodiments, the pharmaceutical composition may comprise from about 5% to about 20% of a co-solvent such as ethanol. The pharmaceutical composition may include a tonicity-adjusting agent, at least one antimicrobial agent and/or a co-solvent such as ethanol.

In embodiments, the pharmaceutical composition is a non-extended release formulation comprising or consisting essentially of buprenorphine at 1.8 mg/mL to 2.4 mg/mL to provide the amount of about 0.12 mg/kg of total mammal body weight. In embodiments, the pharmaceutical composition is a non-extended release formulation comprising or consisting essentially of buprenorphine at 1.8 mg/mL to 2.4 mg/mL to provide the amount of about 0.24 mg/kg of total mammal body weight.

One or more buffers are added to adjust the pH of the formulation to a range of about 3 to about 5. In embodiments, 5-15 mM buffer is added to adjust the pH of the formulation to about 4.0.

The pharmaceutical composition may be administered twice per day, once per day, every other day, every two days, or every 48 hours. In embodiments, the pharmaceutical composition is administered once per day.

DETAILED DESCRIPTION

Figure 1:
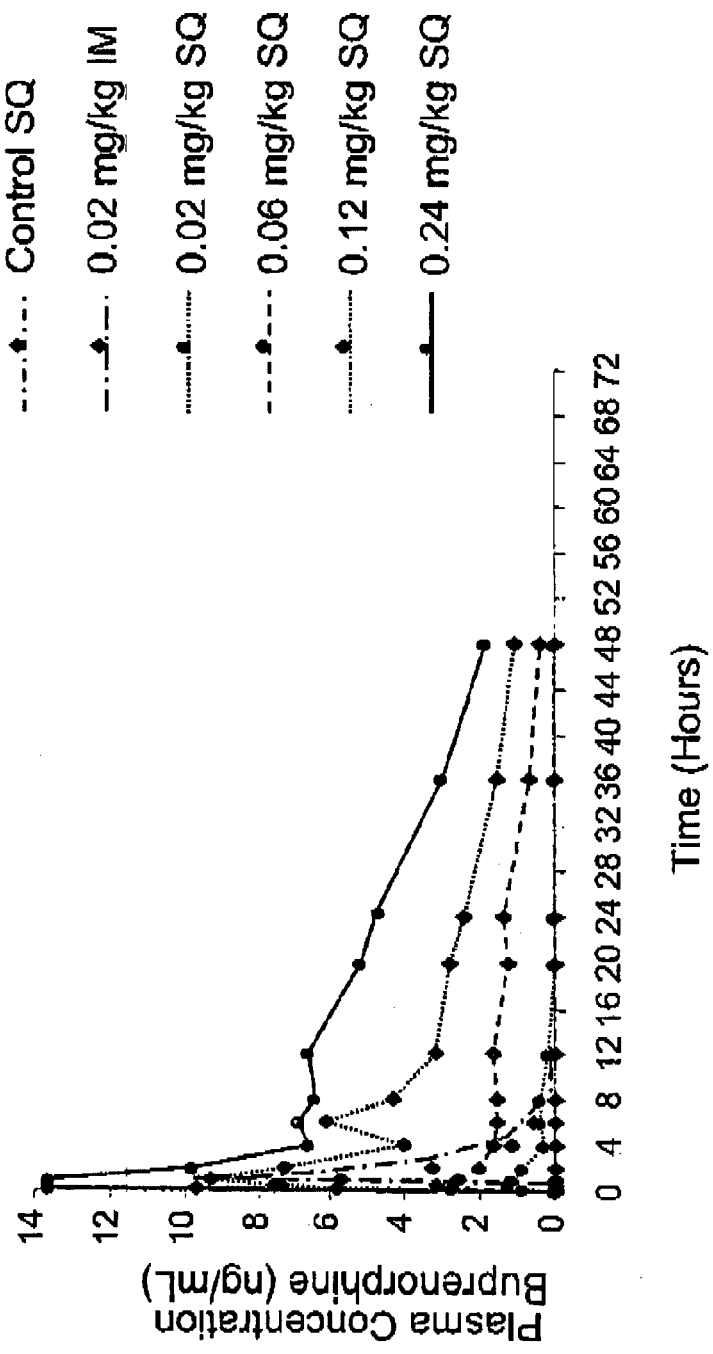
FIG. 1 is a graph illustrating the buprenorphine plasma concentration over time for multiple doses of buprenorphine administered intravenously and subcutaneously, including 0.02 mg/kg intravenous dosing, 0.02 mg/kg subcutaneous dosing, 0.06 mg/kg subcutaneous dosing, 0.12 mg/kg subcutaneous dosing, and 0.24 mg/kg subcutaneous dosing.
Figure 2:
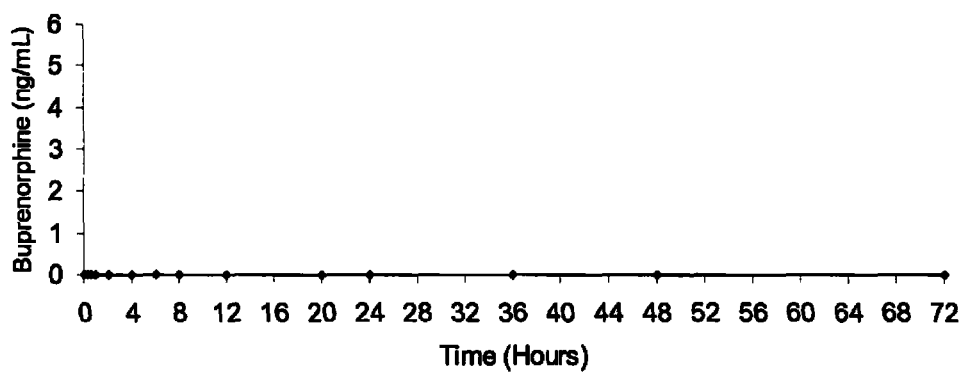
FIG. 2 is a graph illustrating mean buprenorphine plasma concentration following subcutaneous administration of saline.
Figure 3:
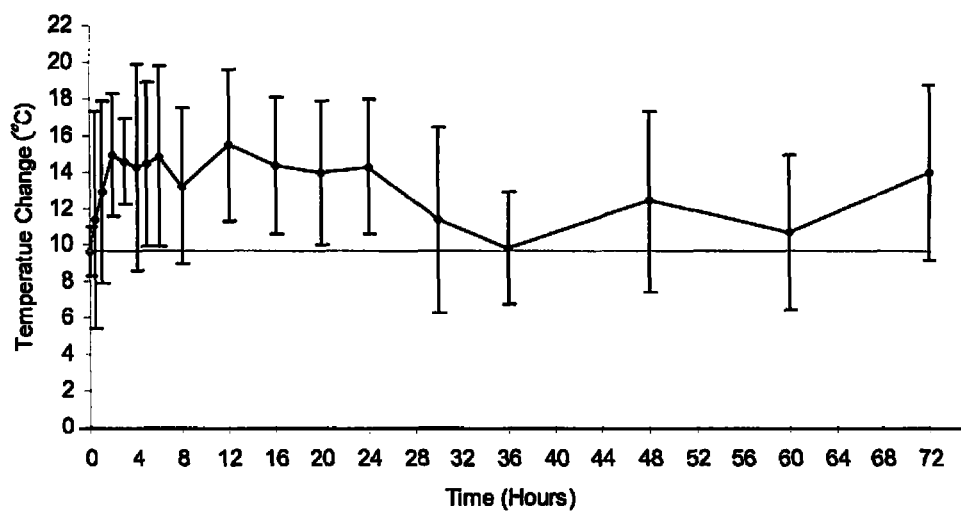
FIG. 3 is a graph illustrating the mean thermal threshold following subcutaneous administration of saline.
Figure 4:
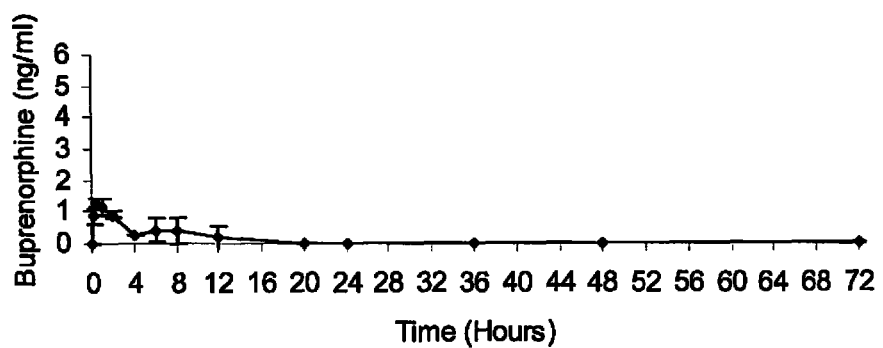
FIG. 4 is a graph illustrating the mean buprenorphine plasma concentration following subcutaneous administration of Buprenex® at 0.02 mg/kg (0.3 mg/mL).
Figure 5:
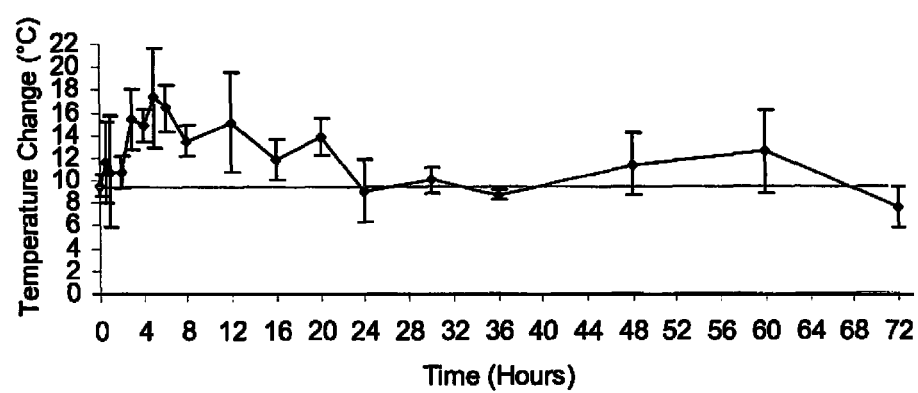
FIG. 5 is a graph illustrating the mean thermal threshold following subcutaneous administration of Buprenex® at 0.02 mg/kg (0.3 mg/mL).
Figure 6:
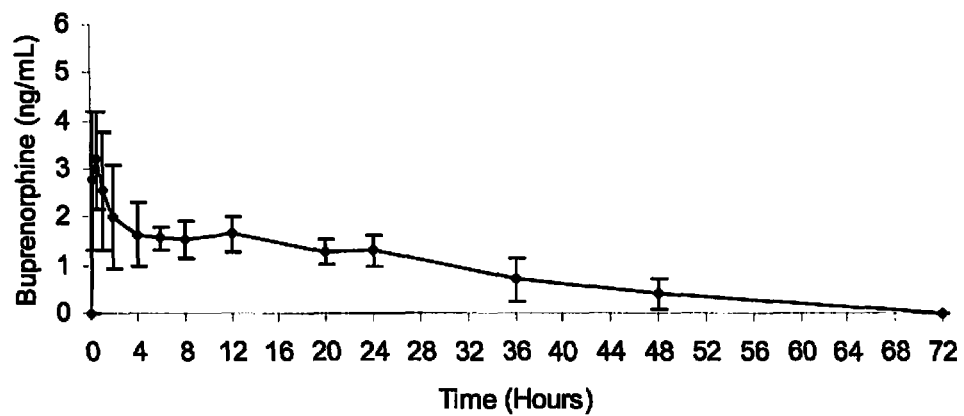
FIG. 6 is a graph illustrating the mean buprenorphine plasma concentration following subcutaneous administration of preserved buprenorphine solution at 0.06 mg/kg (1.2 mg/mL).
Figure 7:
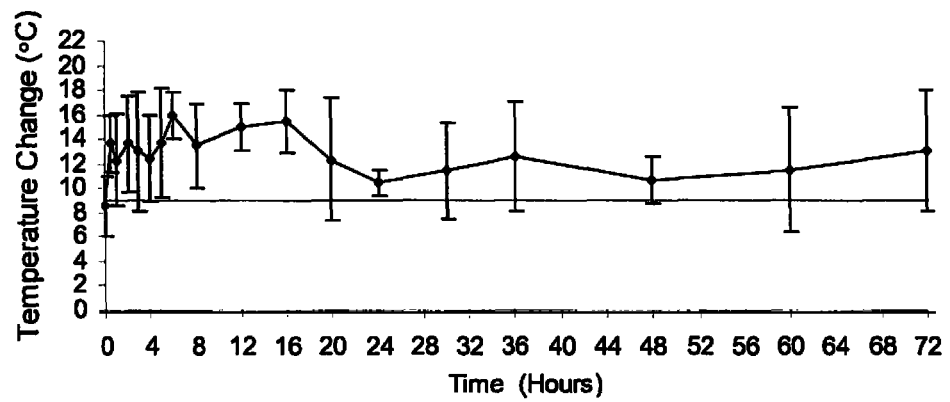
FIG. 7 is a graph illustrating the mean thermal threshold following subcutaneous administration on preserved buprenorphine solution at 0.06 mg/kg (1.2 mg/mL).
Figure 8:
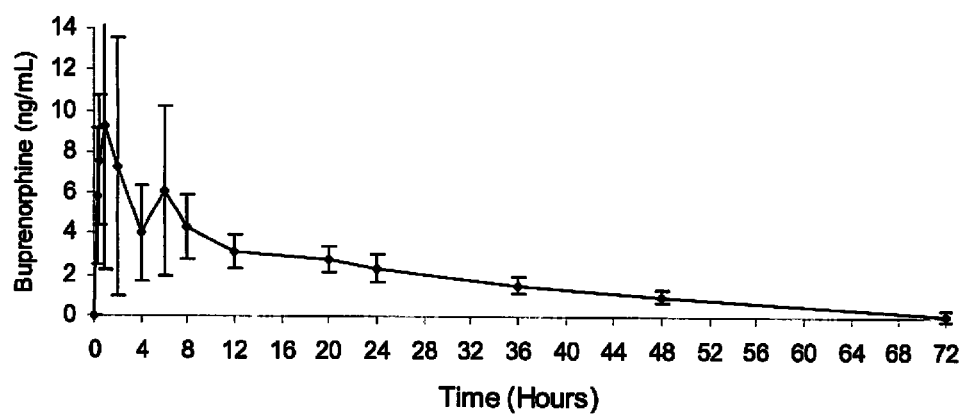
FIG. 8 is a graph illustrating the mean buprenorphine plasma concentration following subcutaneous administration of preserved buprenorphine solution at 0.12 mg/kg (1.2 mg/mL).

The present disclosure is directed to compositions and methods of providing prolonged analgesia to a mammal. Specifically, the compositions and methods of the present disclosure include a single high dose of buprenorphine which is administered to mammals to provide adequate analgesia for at least twelve hours. As used herein, "adequate analgesia" refers to a pain controlled state of a mammal that is assessed by an animal caregiver according to routine techniques or established criteria to make the assessment. For example, adequate analgesia may be assessed by clinical observations such as assessing whether the mammal appears to be comfortable; whether the mammal appears content and quiet when unattended; whether the mammal appears interested in or curious in its surroundings; whether the mammal is interested in the assessor when approaching its cage; whether the mammal seeks attention when the cage is approached and the door opened; whether the mammal exhibits minimal body tension when stroked; whether the mammal exhibits a normal or mild response when palpated at a surgery site; or whether the mammal is not bothered by palpation at a surgery site or palpation at any other location on its body.

Alternatively, or in addition to clinical observation, adequate analgesia may be assessed using thermal threshold techniques which determine whether a mammal is able to tolerate an increase in its reaction skin temperature when compared to its baseline skin temperature (which is known as its thermal threshold). The thermal threshold of a mammal can be determined using routine techniques known in the art. For example, in felines, thermal threshold can be determined using a device as described by Dixon in "A thermal threshold testing device for evaluation of analgesics in cats." *Res Vet Sci* 2002; 72 (3): 205-210 which is incorporated herein by reference.

As used herein, the term "buprenorphine" means an opioid drug having the chemical name, 9α-cyclopropylmethyl-4,5-epoxy-6,14-ethano-3-hydroxy-6-methoxymorphinan-7-yl]-3,3-dimethylbutan-2-ol, or salts or derivatives thereof. Buprenorphine may comprise the free base or pharmaceutically acceptable salts, such as an acid addition salt or a salt with a base. Suitable examples of pharmaceutically acceptable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate(embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. In embodiments, the pharmaceutically acceptable salt includes hydrochloride, sulfate, methane sulfonate, stearate, tartrate, and lactate salts. In embodiments, buprenorphine comprises the acid addition salt, buprenorphine hydrochloride.

The disclosed compositions and methods comprise a high dose of buprenorphine. Generally, the term "high-dose" refers to any dose of buprenorphine greater than conventional doses of about 0.01 mg/kg to about 0.02 mg/kg of total body weight of the mammal. Accordingly, a high-dose of buprenorphine constitutes a dose of buprenorphine in the range of about 0.04 mg/kg to about 2.0 mg/kg of total mammal weight. In embodiments, the high dose of buprenorphine is in the range of about 0.1 mg/kg to about 1 mg/kg of total mammal weight, or in the range of about 0.15 mg/kg to about 0.5 mg/kg of total mammal weight, or in the range of about 0.2 mg/kg to about 0.3 mg/kg of total mammal weight. In embodiments, high dose buprenorphine is about 0.1 mg/kg of total mammal body weight. In embodiments, high dose buprenorphine is about 0.2 mg/kg of total mammal body weight. In embodiments, high dose buprenorphine is about 0.3 mg/kg of total mammal body weight. In embodiments, high dose buprenorphine is about 0.4 mg/kg of total mammal body weight. In embodiments, high dose buprenorphine is about 0.5 mg/kg of total mammal body weight. In embodiments, high dose buprenorphine is about 0.6 mg/kg of total mammal body weight. In embodiments, high dose buprenorphine is about 0.7 mg/kg of total mammal body weight. In embodiments, high dose buprenorphine is about 0.8 mg/kg of total mammal body weight. In embodiments, high dose buprenorphine is about 0.9 mg/kg of total mammal body weight. In embodiments, high dose buprenorphine is about 1.0 mg/kg of total mammal body weight. In embodiments, high dose buprenorphine is about 1.1 mg/kg of total mammal body weight. In embodiments, high dose buprenorphine is about 1.2 mg/kg of total mammal body weight. In embodiments, high dose buprenorphine is about 1.3 mg/kg of total mammal body weight. In embodiments, high dose buprenorphine is about 1.4 mg/kg of total mammal body weight. In embodiments, high dose buprenorphine is about 1.5 mg/kg of total mammal body weight. In embodiments, high dose buprenorphine is about 1.6 mg/kg of total mammal body weight. In embodiments, high dose buprenorphine is about 1.7 mg/kg of total mammal body weight. In embodiments, high dose buprenorphine is about 1.8 mg/kg of total mammal body weight. In embodiments, high dose buprenorphine is about 1.9 mg/kg of total mammal body weight. In embodiments, high dose buprenorphine is about 2.0 mg/kg of total mammal body weight.

Although veterinarians would expect initial plasma levels of buprenorphine administered at a high dose to be greater than plasma levels of buprenorphine administered at a lower dose, Applicants have surprisingly found that administration of high dose buprenorphine retains therapeutic plasma levels for a longer period of time than expected. In particular, Applicants have surprisingly found that administration of high dose buprenorphine retains therapeutic plasma levels for a period of at least 12 hours rather than periods of only 2-8 hours.

In addition, veterinarians would expect a high dose of buprenorphine to cause adverse side effects in mammals such as severe sedation, respiratory depression, cardiovascular effects, anorexia, dysphoria, and hyperexcitability, and therefore, would refrain from administering a high dose. Applicants, however, have surprisingly found that administration of high dose buprenorphine does not cause observable side effects in mammals and have demonstrated its safe use in mammals for the treatment of pain. Additionally, the disclosed compositions and methods enable less frequent administration of buprenorphine resulting in less stress and agitation to the mammal.

As used herein, the term "mammal" may generally be defined as a class of vertebrates, in which the females are characterized by the possession of mammary glands, and both males and females are characterized by sweat glands, hair and/or fur, three middle ear bones used in hearing, and a neocortex region in the brain. The methods of the current disclosure are typically directed to the administration of buprenorphine to domestic and companion animals. Examples of mammals that may be treated with the current disclosure include, but are not limited to canines, felines, pigs, cows, horses, sheep, donkeys, and mules. In a one embodiment, the method of the current disclosure is directed to the treatment of companion animals such as canines and felines. In another embodiment, the method comprises treatment of felines.

The disclosed methods include administering the high dose buprenorphine by a parenteral route of administration. Parenteral administration generally comprises all routes of administration wherein the active ingredient is absorbed systemically by means of piercing the skin or through a mucous membrane, and does not encompass rectal absorption or absorption through the digestive tract (i.e., oral administration). Non-limiting examples of parenteral routes of administration include intradermal, subcutaneous, intercavernous, intravitreal, transscleral, intravenous, intramuscular, intracardiac, intraosseous, and intraperitoneal administrations. In embodiments, the high dose buprenorphine is administered to the mammal by subcutaneous administration. In embodiments, the high dose buprenorphine is administered to the mammal by intramuscular administration.

In embodiments, a single high dose of buprenorphine is administered to a mammal during a period ranging from about 12 hours to about 72 hours providing adequate analgesia to the mammal for a period ranging from about 12 hours to about 48 hours. The disclosed methods include administering a single high dose of buprenorphine to a mammal twice per day, once per day, every 36 hours, every other day, every two days, every 48 hours, every three days, or every 72 hours. In embodiments, the disclosed methods include administering a single high dose of buprenorphine once per day. In embodiments, the disclosed methods include administering a single high dose of buprenorphine once every 36 hours. In embodiments, the disclosed methods include administering a single high dose of buprenorphine once every 48 hours. In embodiments, the disclosed methods include administering a single high dose of buprenorphine once every 72 hours.

The present disclosure is also directed to pharmaceutical compositions or formulations that comprise or consist essentially of buprenorphine and at least one pharmaceutically acceptable excipient. In embodiments, a single composition comprises the single high dose of buprenorphine. In embodiments, a single composition consists essentially of the single high dose of buprenorphine.

Pharmaceutically acceptable excipients used in the composition or formulations of the present invention may be excipients involved in enabling buprenorphine to be administered by a parenteral route of administration. Pharmaceutically acceptable excipients may include, but are not limited to, solvent systems, solubilization agents, stabilization agents, tonicity-adjusting agents, antimicrobial preservative agents and combinations thereof.

Suitable solvent systems may include solvents and oils. Suitable solvents may include, but are not limited to, propylene glycol, glycerin, ethanol, polyethylene glycol 300, polyethylene glycol 400, sorbitol, dimethylacetamide, Cremophor EL, dimethylacetamide, N-methyl-2-pyrrolidone, and mixtures thereof. Suitable examples of oils include sesame, soybean, corn, castor, cottonseed, peanut, arachis, ethyl oleate, isopropyl myristate, glycofurol, petrolatum, and combinations thereof.

Solubilization agents may include surfactants and complexation agents. Non-limiting examples of surfactants include polyoxyethylene sorbitan monooleate (Tween 80), sorbitan monooleate, polyoxyethylene sorbitan monolaurate (Tween 20), lecithin, polyoxyethylene-poloxypropylene copolymers (Pluronics®), and combinations thereof. Suitable examples of complexation agents include, but are not limited to, hydroxypropyl-β-cyclodextrin, sulfobutylether-β-cyclodextrin (Captisol®), polyvinylpyrrolidone, arginine, lysine, histidine, and combinations thereof.

Stabilization agents may comprise buffers, antioxidants, chelating agents and combinations thereof. Suitable buffers may include, for example, acetate, citrate, tartrate, phosphate, triethanolamine (TRIS) and combinations thereof. One or more buffers are added to adjust the pH of the formulation to a range of about 3 to about 5. In embodiments, 5-15 mM buffer is added to adjust the pH of the formulation to about 4.0. Suitable antioxidants may include, for example, ascorbic acid, acetylcysteine, sulfurous acid salts, such as bisulfite and metabisulfite, monothioglycerol, and combinations thereof. Suitable chelating agents may include ethylenediaminetetraacetic acid (EDTA), sodium citrate and combinations thereof.

Tonicity-adjusting agent may be used in the disclosed compositions to reduce irritation to the body tissue at the injection site. Suitable tonicity-adjusting agents include, for example, sodium chloride, glycerin, mannitol, dextrose and combinations thereof. Dextrose anhydrous, for example, may be present in the formulation in the amount of about 10 mg/mL to about 100 mg/mL or about 30 mg/mL to about 70 mg/mL or about 1% to about 10% or about 3% to about 7%.

Antimicrobial agents may be used in the disclosed compositions to prevent microbial growth in the aqueous environment of the formulation. Suitable antimicrobial agents may include, for example, phenol, meta-cresol, benzyl alcohol, parabens, benzalkonium chloride, chlorobutanol, thimerosal, phenylmercuric acids such as acetate, borate, and nitrate, and combinations thereof. Antimicrobial agents may be present in the formulation at any suitable amount. Methyl paraben, for example, may be present in the formulation in the amount of about 0.1 mg/ml to about 3.0 mg/ml or about 0.4 mg/mL to about 2.4 mg/mL or about 0.02 to about 0.3% or about 0.04 to about 0.24%. Propyl paraben, for example, may be present in the formulation in the amount of about 0.01 mg/ml to about 0.5 mg/ml or about 0.05 mg/mL to about 0.3 mg/mL or about 0.005% to about 0.05% or about 0.01% to about 0.03%. Chlorocresol, for example, may be present in the formulation in the amount of about about 0.36 mg/mL to about 1.5%. Benzyl alcohol, for example, may be present in the formulation in the amount of about 0.5% to about 3% or about 0.9% to about 2%.

Solvents may be used in the disclosed compositions as co-solvents and/or preservatives. Suitable solvents may include water and alcohols such as, for example, ethanol. Solvents may be present in the formulation at any suitable amount. Ethanol, for example, may be present in the formulation in the amount of from about 2 to about 30% (v/v) or from about 5 to about 20% (v/v). In embodiments, the amount of ethanol is about 10%.

In embodiments, the pharmaceutical composition comprises buprenorphine, a tonicity-adjusting agent (such as dextrose) in an amount of from about 3% to about 7% (v/v), and at least one antimicrobial agent (such as methylparaben, propylparaben or combinations thereof) in an amount of from about 0.05 mg/mL to about 2.5 mg/mL. In embodiments, the pharmaceutical composition comprises buprenorphine, a tonicity-adjusting agent (such as dextrose) in an amount of from about 3% to about 5% (v/v), and at least one antimicrobial agent (such as methylparaben, propylparaben or combinations thereof) in an amount of from about 0.05 mg/mL to about 2.5 mg/mL.

The disclosed compositions and formulations may be "non-extended" or "immediate" release formulations of buprenorphine. Non-extended release formulations refer to formulations that do not rely on other excipients to delay the release of the buprenorphine from the composition or formulation. The non-extended release formulations do not include components of sustained release formulations such as microparticles, polymer matrix systems, fat emulsions, microspheres, oil in water emulsions, and the like.

The buprenorphine and formulation excipients described above may be present in a formulation in any suitable amount. Tables 1A and 1B list non-limiting examples of suitable amounts of buprenorphine and particular excipients as concentration and percentage by volume of the formulation.

TABLE 1A

| Components | Concentration | Percent (v/v) | Function |
|---|---|---|---|
| Buprenorphine HCl | 0.8 mg/mL-2.4 mg/mL | 0.08-0.24% | active substance |
| Dextrose anhydrous | 30-70 mg/mL | 3-7% | tonicity agent |
| Methyl paraben | 0.4-2.4 mg/mL | 0.04-0.24% | preservative |
| Propyl paraben | 0.05-0.3 mg/mL | 0.01-0.03% | preservative |
| Sodium Acetate Trihydrate | 5-15 mM | | buffer |
| Acetic Acid | | | buffer |
| Ethanol | 50-20 mg/mL | 5-20% | co-solvent/preservative |
| HCl or NaOH | as needed | as needed | pH adjustment |
| Water for Injection | | | solvent |

The following formulation is a non-limiting example of a suitable high dose buprenorphine formulation:

TABLE 1B

| Components | Amount, mg | Percent | Function |
|---|---|---|---|
| Buprenorphine HCl (free base equivalent) | 1.8 | 0.18 | active agent |
| Dextrose anhydrous | 50.0 | 5.0 | tonicity agent |
| Methyl paraben | 1.8 | 0.18 | preservative |
| Propyl paraben | 0.2 | 0.02 | preservative |
| Sodium acetate trihydrate | 0.2 | 0.02 | buffer |
| Acetic acid | 0.5 | 0.05 | buffer |
| Ethanol | 100.0 | 10.0 | co-solvent/preservative |
| HCl or NaOH | as needed | as needed | pH adjustment to approximately pH 4.0 |
| Water | up to 1 ml | | solvent |

The dose volume of buprenorphine in a formulation may depend on the buprenorphine solution concentration and the buprenorphine dose. For example, in order to control the volume administered to the mammal when higher doses of buprenorphine are administered, the buprenorphine concentration may be increased. As presented in Table 1C below, a dose volume of 0.075 mL/kg may be used to deliver a dose of 0.06 mg/kg at a concentration of 0.8 mg/mL; a dose volume of 0.033 mL/kg may be used to deliver a dose of 0.06 mg/kg at a concentration of 1.8 mg/mL; a dose volume of 0.025 mL/kg may be used to deliver a dose of 0.06 mg/kg at a concentration of 2.4 mg/mL; a dose volume of 0.3 mL/kg may be used to deliver a dose of 0.24 mg/kg at a concentration of 0.8 mg/mL; a dose volume of 0.13 mL/kg may be used to deliver a dose of 0.24 mg/kg at a concentration of 1.8 mg/mL; a dose volume of 0.1 mL/kg may be used to deliver a dose of 0.24 mg/kg at a concentration of 2.4 mg/mL; a dose volume of 0.2 mL/kg may be used to deliver a dose of 0.48 mg/kg at a concentration of 2.4 mg/mL; a dose volume of 0.3 mL/kg may be used to deliver a dose of 0.72 mg/kg at a concentration of 2.4 mg/mL; a dose volume of 1.25 mL/kg may be used to deliver a dose of 1.0 mg/kg at a concentration of 0.8 mg/mL; a dose volume of 0.56 mL/kg may be used to deliver a dose of 1.0 mg/kg at a concentration of 1.8 mg/mL; and a dose volume of 0.42 mL/kg may be used to deliver a dose of 1.0 mg/kg at a concentration of 2.4 mg/mL. In embodiments a buprenorphine dose volume of 0.13 mL/kg may be used to deliver a buprenorphine dose of 0.24 mg/kg at a concentration of 1.8 mg/mL.

TABLE 1C

| Dose Volume (mL/kg) | Dose (mg/kg) | Concentration (mg/mL) |
|---|---|---|
| 0.075 | 0.06 | 0.8 |
| 0.033 | 0.06 | 1.8 |
| 0.025 | 0.06 | 2.4 |
| 0.3 | 0.24 | 0.8 |
| 0.13 | 0.24 | 1.8 |
| 0.1 | 0.24 | 2.4 |
| 0.2 | 0.48 | 2.4 |
| 0.3 | 0.72 | 2.4 |
| 1.25 | 1.0 | 0.8 |
| 0.56 | 1.0 | 1.8 |
| 0.42 | 1.0 | 2.4 |

The disclosed compositions may be administered during a period ranging from about 12 hours to about 48 hours. The disclosed compositions may be administered twice per day, once per day, every other day, every two days, or every 48 hours. In embodiments, the disclosed composition is administered once per day.

The disclosed compositions and methods provide adequate analgesia over a prolonged period of time. The term "prolonged" refers to a period of at least about 12 hours, a period of from about 12 hours to about 72 hours, or a period of from about 24 hours to about 48 hours. In embodiments, the disclosed compositions and methods provide adequate analgesia for up to about 72 hours. It should be appreciated that the duration of pain relief will vary depending on the pain tolerance of the mammal in need of pain relief.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the present disclosure in detail, the same will be more clearly understood by reference to the following examples, which are included for purposes of illustration only and are not intended to be limiting of the disclosure.

EXAMPLES

In the examples below, the mammals studied were adult cats. The cats were housed individually. Fresh food and water was provided ad libitum. Cats were weighed prior to dosing. Body weights were used to calculate dose volumes administered. Cats were dosed on a per kilogram basis.

A number of different buprenorphine formulations were used in the examples. One buprenorphine formulation used was Buprenex® (buprenorphine), which is a commercially available non-buffered injectable 0.3 mg/mL solution labeled for human use (Reckitt Benckiser Pharmaceuticals Inc.). Other non-extended release buprenorphine formulations used include formulations containing buprenorphine as well as 5% dextrose, 2.3 mg/mL methylparaben and 0.3 mg/mL propylparaben at a pH of 5.2. Another formulation contained buprenorphine, 5% dextrose, 10% ethanol, 1.8 mg/mL methylparaben, 0.2 mg/mL propylparaben and an 10 mM acetate buffer at a pH of 5.2. Other formulations contained buprenorphine as well as 5% dextrose at a pH of 4.7, 5.4, 6.11 or 6.28.

Example 1

Buprenorphine Plasma Concentration Over Time for Cats

Buprenex® was used in the following examples. A syringe with a 22 g needle was filled with the appropriate volume of buprenorphine or control and was administered by subcutaneous injection at the base of the neck between the shoulder blades.

Blood samples were collected prior to buprenorphine administration and at approximately 0.25, 0.5, 1, 2, 4, 6, 8, 12, 20, 24, 36, 48 and 72 hours following dosing. Blood samples were collected by direct jugular venipuncture into a vacutainer containing lithium heparin. Volume of each sample was approximately 1.5 mL. Blood samples were placed immediately on ice and centrifuged at approximately 4° C. for approximately 15 minutes at approximately 3000 rpm for plasma preparation. Plasma samples were immediately frozen on dry ice and stored at −70° C. until analysis.

As set forth in Table 2, six treatment groups were monitored to determine the plasma profile for various routes of administration and dosing.

TABLE 2

| Group | Number of Animals | Route of Admin | Formulation |
|---|---|---|---|
| 1 | 6 | SQ | placebo (saline) |
| 2 | 3 | IM | 0.02 mg buprenorphine |
| 3 | 3 | SQ | 0.02 mg buprenorphine |
| 4 | 6 | SQ | 0.06 mg buprenorphine |
| 5 | 6 | SQ | 0.12 mg buprenorphine |
| 6 | 6 | SQ | 0.24 mg buprenorphine |

The first group consisted of a control group, in which six cats were administered placebo (saline) subcutaneously (hereinafter "control SQ"). In the second group, a total of three cats were administered 0.02 mg of buprenorphine per kilogram of body weight by the intramuscular route of administration (hereinafter "0.02 mg/kg IM"). In the third group, a total of three cats were administered 0.02 mg of buprenorphine per kilogram of body weight by the intramuscular route of administration (hereinafter "0.02 mg/kg SQ"). In the fourth group, a total of six cats were administered 0.06 mg of buprenorphine per kilogram of body weight by the intramuscular route of administration (hereinafter "0.06 mg/kg SQ"). In the fifth group, a total of six cats were administered 0.12 mg of buprenorphine per kilogram of body weight by the intramuscular route of administration (hereinafter "0.12 mg/kg SQ"). In the final group, a total of six cats were administered 0.24 mg of buprenorphine per kilogram of body weight by the intramuscular route of administration (hereinafter "0.24 mg/kg SQ").

Regardless of the treatment group, plasma was drawn from each cat in the group every four hours, for a period of 48 hours, and tested to determine the buprenorphine concentration in mg/mL. The results of the plasma profile study are set forth in FIG. 1 demonstrating the effectiveness of the disclosed methods of treatment. In particular, FIG. 1 illustrates that the Control SQ, 0.02 mg/kg IM, and 0.02 mg/kg SQ treatment groups showed buprenorphine plasma concentrations that were negligible after approximately 8 hours. In contrast, however, the 0.06 mg/kg SQ, 0.12 mg/kg, and 0.24 mg/kg SQ treatment groups showed effective buprenorphine plasma concentrations 24 hours after the initial dosing. No significant side effects were noted in the study animals, such as a change in heart and respiration rates.

Example 2A

Dose Characterization

Studies were conducted to evaluate the efficacy on duration of analgesia of a non-extended release buprenorphine injectable solution administered at higher than conventional doses. Thermal threshold studies and surgical studies were performed to evaluate the efficacy of the non-extended release high dose buprenorphine injectable solution. Five studies were conducted in which eight treatment groups were evaluated.

The primary objective of these studies was to determine analgesic effects of buprenorphine injectable solutions in cats at subcutaneous doses of: 0 (saline), 0.02, 0.06, 0.12, and 0.24 mg/kg. Additional studies were done to determine if the concentration of the buprenorphine injectable solution influenced analgesia. The concentration of the buprenorphine injectable solution was increased from 0.3 mg/mL to 1.2 mg/mL, and the dose volume was maintained at about 0.03 to 0.2 mL/Kg. Furthermore, the dose of 0.12 mg/kg was evaluated at the concentrations of: 0.3 mg/mL, 0.6 mg/mL and 1.2 mg/mL.

Treatment groups are summarized in Table 4. Treatment Group 1 is included because 0.02 mg/kg is the most common dose recommended in the literature for post-operative pain in cats. Cats were administered a subcutaneous dose of buprenorphine or control article. Effectiveness was evaluated by determining the thermal threshold of each cat at prescribed time points. Blood samples were collected at prescribed time points for determination of buprenorphine plasma concentrations.

TABLE 4

Treatment Groups

| Group | Number of Cats | Dose Level (mg/kg) | Buprenorphine Concentration (mg/mL) | Formulation |
|---|---|---|---|---|
| 1 | 6 | Saline | N/A | Physiologic Saline |
| 2 | 3 | 0.02 | 0.3 | Buprenex ® |
| 3 | 6 | 0.06 | 1.2 | Buprenorphine HCl in 5% dextrose 2.3 mg/mL methlyparaben 0.3 mg/mL propylparaben pH = 5.2 |
| 4 | 6 | 0.12 | 1.2 | Buprenorphine HCl in 5% dextrose 2.3 mg/mL methlyparaben 0.3 mg/mL propylparaben pH = 5.2 |
| 5 | 6 | 0.24 | 1.2 | Buprenorphine HCl in 5% dextrose 2.3 mg/mL methlyparaben 0.3 mg/mL propylparaben pH = 5.2 |
| 6 | 3 | 0.12 | 0.3 | Buprenex ® |
| 7 | 3 | 0.12 | 0.6 | Buprenorphine HCl in 5% dextrose pH = 6.28 |
| 8 | 3 | 0.12 | 1.2 | Buprenorphine HCl in 5% dextrose pH = 6.11 |

Thermal threshold studies were conducted and buprenorphine plasma concentrations were determined at prescribed time points. Thermal threshold was determined using the device as described by Dixon in "A thermal threshold testing device for evaluation of analgesics in cats." *Res Vet Sci* 2002; 72 (3): 205-210 which is incorporated herein by reference. Thermal stimulation was provided by a probe that was held in position on the cat's shaved thorax by a pressure bladder connected to an elastic band. This ensured there was consistent contact between the probe and the cat's skin. The temperature rise of the probe was 0.6° C./second with a safety cut-off at 55° C. Each cat received five baseline threshold stimulations prior to dose administration, and following administration at: 0.5, 1, 2, 3, 4, 5, 6, 8, 12, 16, 20, 24, 30, 36, 48, 60, and 72 hours. Starting skin temperature, reaction skin temperature and the type of reaction indicating a response to the increased temperature was recorded at each threshold evaluation.

Mean buprenorphine plasma concentrations and mean thermal threshold data are presented in FIGS. 2-17. Thermal threshold data is presented as the difference between the starting and reaction skin temperature. If the test article provided analgesia, the temperature at which the cat reacted was increased compared to baseline. A horizontal line, which corresponds to the baseline temperature that the cat reacted to, is included in the figures so differences between baseline and results after test article administration are easier to distinguish. Three to six cats were used in each treatment group. Results are presented as the mean±standard deviation.

As illustrated in FIGS. 3, 5, 7, 9, 11, 13, 15 and 17, thermal threshold studies indicated the non-extended release high dose buprenorphine injectable solution provided at least 24 hours of analgesia.

As illustrated in Table 5, as the dose increased from 0.02 mg/kg to 0.24 mg/kg, mean peak plasma concentration increased, and buprenorphine remained detectable in the plasma for longer periods of time. It should be appreciated that any variability in the mean buprenorphine plasma levels may be attributed to differences in rates of buprenorphine metabolism or clearance among the study animals.

TABLE 5

Comparison of Mean Buprenorphine Plasma Concentrations of Different Doses

| Dose (mg/kg) | Buprenorphine Concentration of Test Article (mg/mL) | Estimated Peak Plasma Concentration (ng/mL) | Estimated Time to Peak Plasma Concentration (Hours) | Estimated Duration of Detectable Plasma Concentration (Hours) |
|---|---|---|---|---|
| 0.02 | 0.3 | 1.3 | 1 | 12 |
| 0.06 | 1.2 | 3.2 | 0.5 | 48 |
| 0.12 | 1.2 | 9.3 | 1 | 72 |
| 0.24 | 1.2 | 13.6 | 0.5 | 72 |

In addition, different buprenorphine injectable solution concentrations (0.3, 0.6, and 1.2 mg/mL) at a dose of 0.12 mg/kg did not appear to affect thermal threshold.

TABLE 6

Comparison of Mean Buprenorphine Plasma Concentrations
of Different Test Article Buprenorphine Concentrations

| Dose (mg/kg) | Buprenorphine Concentration of Test Article (mg/mL) | Estimated Peak Plasma Concentration (ng/mL) | Estimated Time to Peak Plasma Concentration (Hours) | Estimated Duration of Detectable Plasma Concentration (Hours) |
|---|---|---|---|---|
| 0.12 | 0.3 | 6.6 | 0.5 | 48 |
| 0.12 | 0.6 | 14.8 | 1 | 72 |
| 0.12 | 1.2 | 9.3 | 1 | 72 |

Figure 9:
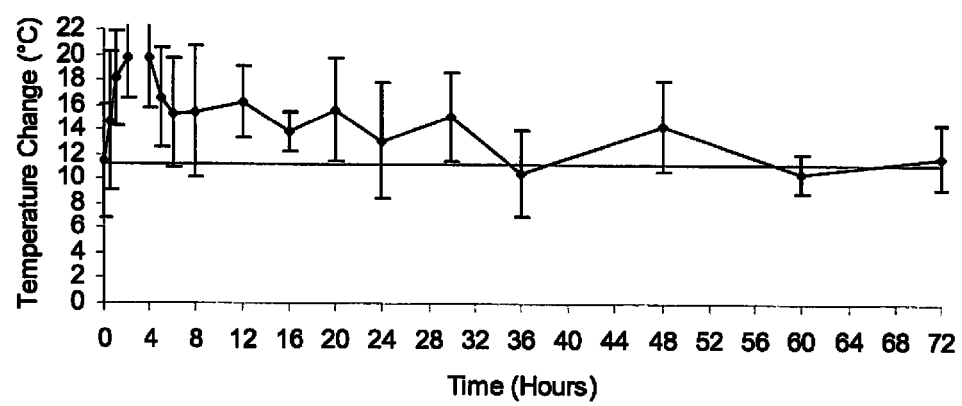
FIG. 9 is a graph illustrating the mean thermal threshold following subcutaneous administration of preserved buprenorphine solution at 0.12 mg/kg (1.2 mg/mL).
Figure 10:
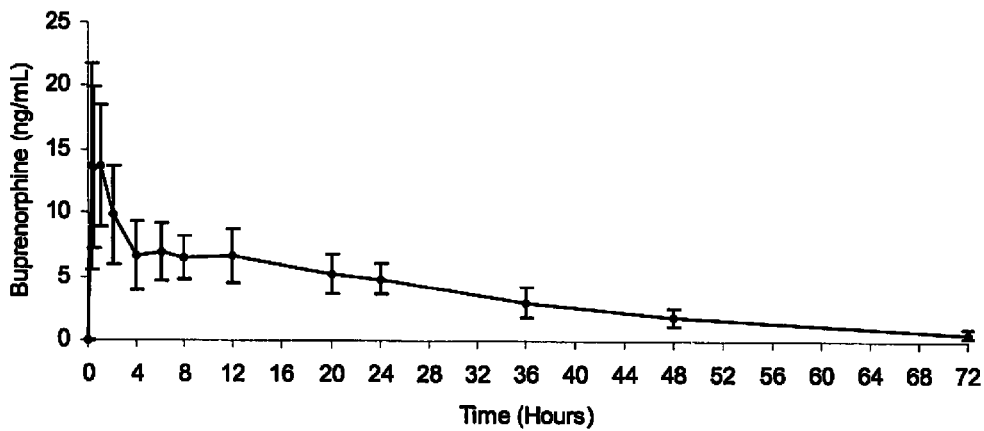
FIG. 10 is a graph illustrating the mean buprenorphine plasma concentration following subcutaneous administration of preserved buprenorphine solution at 0.24 mg/kg (1.2 mg/mL).
Figure 11:
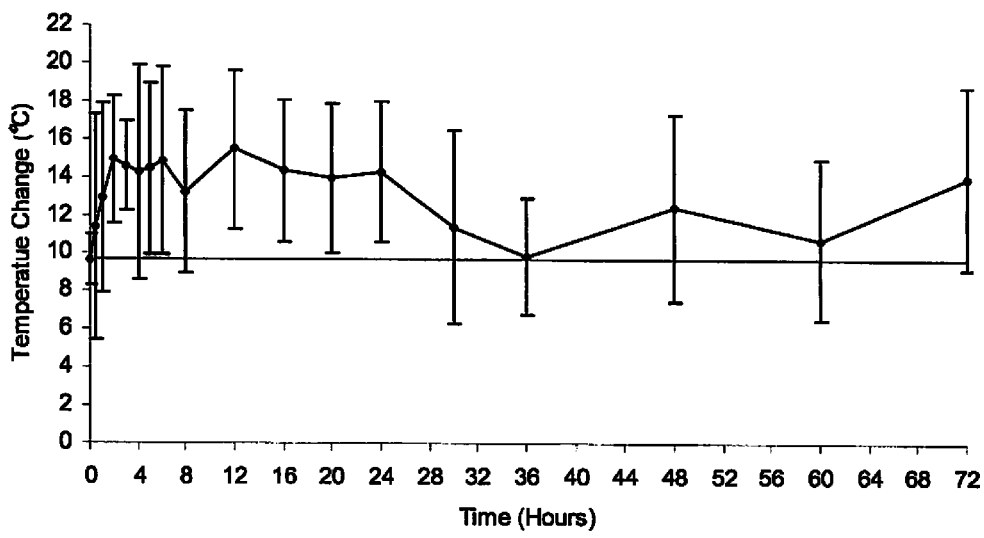
FIG. 11 is a graph illustrating the mean thermal threshold following subcutaneous administration of preserved buprenorphine solution at 0.24 mg/kg (1.2 mg/mL).
Figure 12:
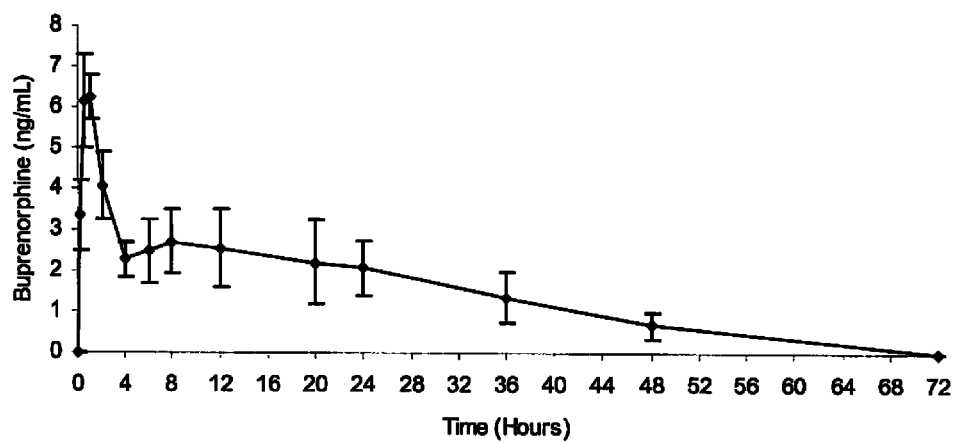
FIG. 12 is a graph illustrating the mean buprenorphine plasma concentration following subcutaneous administration of Buprenex® at 0.12 mg/kg (0.3 mg/mL).
Figure 13:
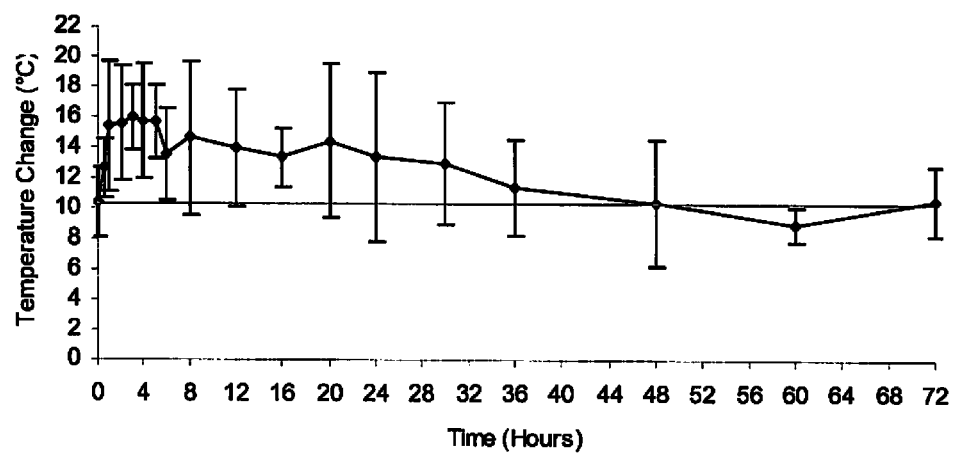
FIG. 13 is a graph illustrating the mean thermal threshold following subcutaneous administration of Buprenex® at 0.12 mg/kg (0.3 mg/mL).
Figure 14:
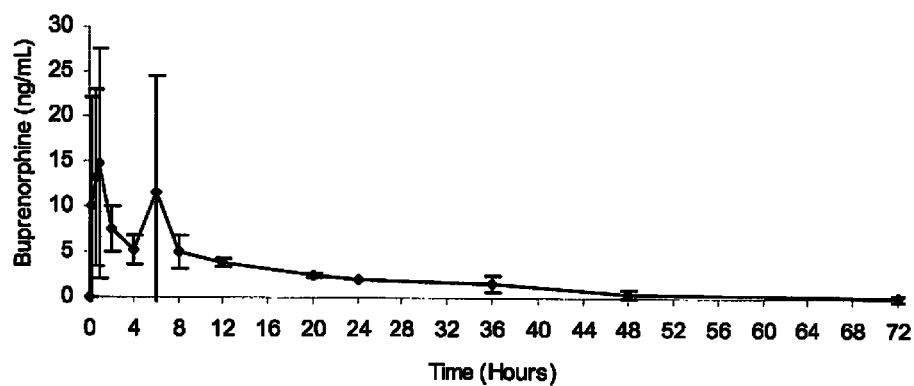
FIG. 14 is a graph illustrating the mean buprenorphine plasma concentration following subcutaneous administration of buprenorphine solution at 0.12 mg/kg (0.6 mg/mL).
Figure 15:
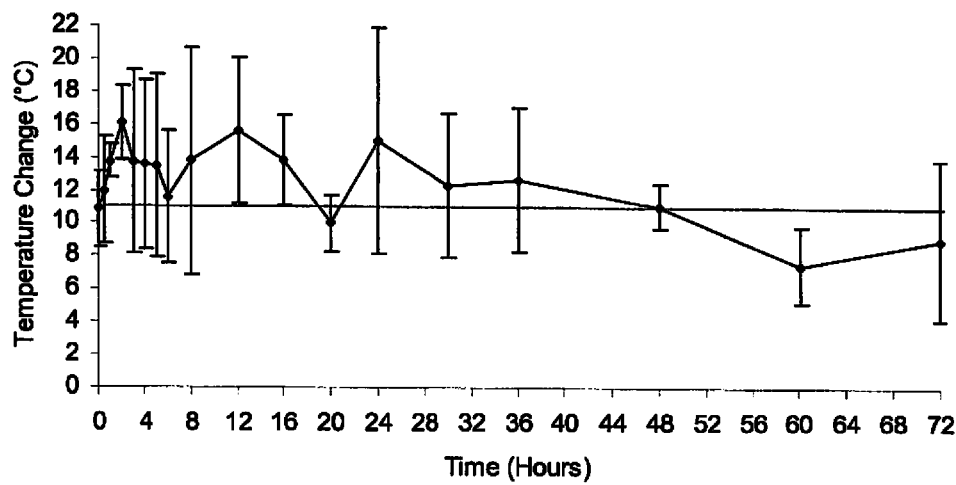
FIG. 15 is a graph illustrating the mean thermal threshold following subcutaneous administration of buprenorphine solution at 0.12 mg/kg (0.6 mg/mL).
Figure 16:
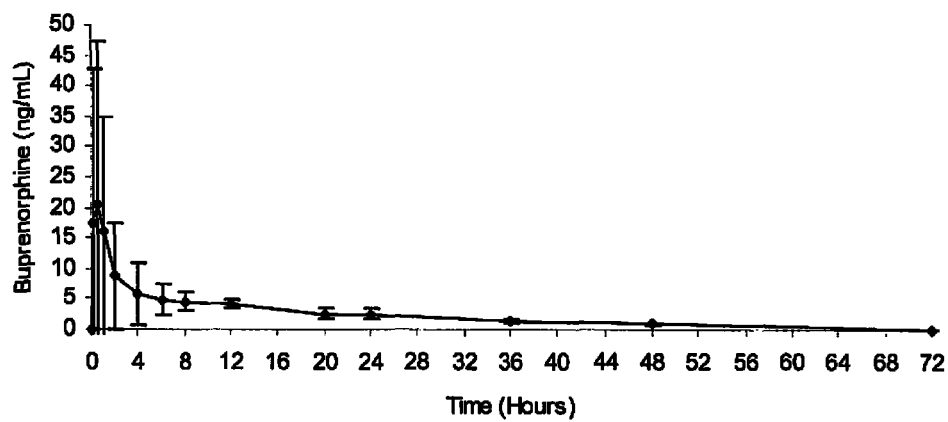
FIG. 16 is a graph illustrating the mean buprenorphine plasma concentration following subcutaneous administration of buprenorphine solution at 0.12 mg/kg (1.2 mg/mL).
Figure 17:
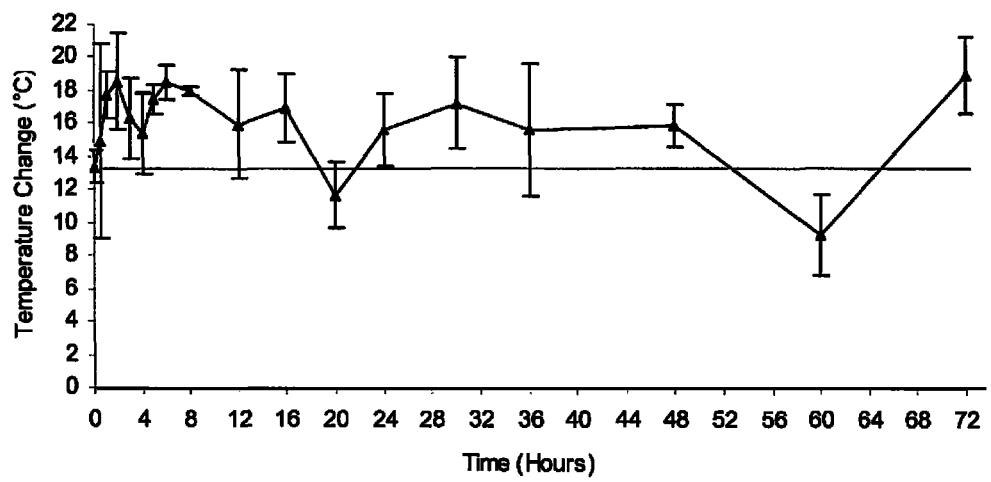
FIG. 17 is a graph illustrating the mean thermal threshold following subcutaneous administration of buprenorphine solution at 0.12 mg/kg (1.2 mg/mL).

Thermal threshold data indicated that higher doses of buprenorphine appear to result in longer analgesia. Buprenorphine administered at 0.02 mg/kg appeared to provide analgesia for approximately 20 hours in this model. When doses were increased, duration of analgesia appeared to increase to 24-28 hours, but there did not appear to be a clear difference between the three higher doses (0.06 mg/kg, 0.12 mg/kg, and 0.24 mg/kg) in this model. All three treatment groups had similar thermal threshold curves (FIGS. 9, 13, and 15). Therefore, a single high dose of a non-extended release buprenorphine formulation appears to have a 24 to 28 hour duration of adequate analgesia.

Example 2B

Administration of Buprenorphine in Cats for Post-Operative Pain Management

Based on foregoing results, and an intended use for high dose buprenorphine for post-operative pain in mammals, surgical studies were performed. The cats studied underwent an ovariohysterectomy or orthopedic (onychectomy) procedure and were monitored to determine the effectiveness of post-operative pain control. The objectives of these studies were to evaluate the ability of a single high dose of a non-extended release buprenorphine formulation to provide at least 24 hours of analgesia following the surgical procedure and to evaluate the ability of buprenorphine to control post-operative pain over 72 hours with three administrations of the formulation 24 hours apart.

Three studies were performed. Study personnel were blinded to treatment. Studies evaluated the ability of non-extended release buprenorphine injectable solution to control post-operative soft tissue or orthopedic pain for 24 hours with a single dose of buprenorphine administered one hour before surgery. Injectable solution was administered one hour prior to induction of anesthesia because thermal threshold data indicated a one hour onset of analgesia following administration. Efficacy of two additional doses, at 24 and 48 hours, to control post-operative pain until 72 hours after the first injection, was also evaluated. Buprenorphine injectable solution was administered at several different doses.

Female and male cats were obtained from local shelters and were identified by ID number provided by the shelter. Cats enrolled in the study were between six months and four years of age, weighed between two and ten kilograms, were non-pregnant and non-lactating, were generally in good health, and had a good disposition that allowed study procedures to be performed. Additionally, the cats had not received any medications within 30 days before study start, or during the study (except antibiotics).

Cats were single-housed in the feline ward of the Veterinary Specialty Center in standard Snyder cages (26 inches deep×21 inches wide×25 inches tall). Fluorescent lighting was on from 8 AM-6 PM. Temperature was controlled remotely and maintained at 65-72° F. Food and water were offered in stainless steel bowls. Cats were allowed to be acclimated to their new surroundings for 24 hours prior to procedures being performed. Prior to administration of medications and surgery, a medical history was provided and a physical exam was performed on each cat.

Three separate groups of cats were administered buprenorphine after an ovariohysterectomy procedure and monitored to determine the effectiveness of post-operative pain control. Specifically, each of the three groups consisted of nine female cats.

Each of the three treatment groups was administered a different dose of buprenorphine by subcutaneous administration. Increased doses of buprenorphine (0.06, 0.12, and 0.24 mg/kg) at a solution concentration of 1.2 or 2.4 mg/mL were used at a dosing interval of 24 hours. The first group received 0.06 mg/kg of total body weight as the total daily dosage amount, the second group received 0.12 mg/kg of total body weight as the total daily dosage amount, and the third group received 0.24 mg/kg of total body weight as the total daily dosage amount. A total of three doses of buprenorphine were administered to each cat in the respective treatment groups at 24-hour intervals for a total of 72 hours.

Buprenorphine and premedications (acepromazine, 0.05 mg/kg SQ and atropine, 0.04 mg/kg SQ) were administered one hour before induction of anesthesia. Buprenorphine and premedications were administered as separate injections. Two more doses of buprenorphine where administered 24 and 48 hours after the first dose. Additionally, a group in which buprenorphine was administered at the conventional dose of 0.02 mg/kg every eight hours for 72 hours was included for comparison. Treatment groups are summarized in Table 4.

Anesthesia was induced with propofol, 4-6 mg/kg intravenously, slowly to effect and the cat was intubated. Anesthesia was maintained with sevoflurane. Sevoflurane concentration was maintained at the appropriate setting to provide a surgical plane of anesthesia throughout surgery. Balanced electrolyte fluids were administered at 10 mL/kg/hr during the surgery to maintain blood pressure. Ovariohysterectomy was performed following current standards of practice using a midline abdominal approach. Onychectomy was performed following current standards of practice, using a scalpel or laser. Each method was used in five cats. If the cat was neutered in addition to the onychectomy, it was done following current standards of practice.

Baseline heart rate and respiratory rate were measured immediately prior to buprenorphine administration and three minutes after anesthesia induction. Heart rate, electrocardiogram, respiratory rate, end-tidal $CO_2$, hemoglobin saturation ($SpO_2$), body temperature, and either indirect or direct blood pressure were monitored at five minute intervals during surgery.

Sedation, excitation, and analgesia/pain were evaluated using a sedation, excitation, & pain scoring procedure. A single person did all assessments for an individual cat. If an assessment time point and drug administration time point coincided the assessment was done prior to the dose being administered. These time points were: 24 and 48 hours.

Baseline (immediately prior to buprenorphine administration) sedation, excitation, and pain/analgesia were measured in each cat. Following surgery, the cat was placed on a towel and continuously monitored in the immediate postoperative period until extubation. The treatment groups were continuously monitored over the course of the 72-hour period to determine if the 24-hour regimen for each group was successful in relieving the pain of the cats. Cats were monitored for sedation, excitation, and postoperative pain/analgesia within 30 minutes of extubation, 2, 4, 8, 12, 16, 20, 24, 32, 48, 56, and 72 hours after test article administration. Free choice cat food and water were offered to the cats four hours after recovery. If at any time during the study (not just the predetermined time points) the assessor thought the cat may be painful, an assessment was performed.

After finishing the sedation, excitation, and pain assessment, the assessor used his/her clinical judgment to determine if the cat needed to be rescued. The first rescue medication administered was meloxicam (0.1 mg/kg SQ). If the first rescue did not provide adequate analgesia, a second rescue was administered (hydromorphone 0.3 mg/kg SQ).

Treatment was considered successful if the cat made it through the entire 72-hour period without needing additional pain medications, other than the three doses of buprenorphine. Conversely, if a cat required rescue during the study period, it was considered a treatment failure. Buprenorphine formulations used in the surgical studies are summarized in Table 7.

TABLE 7

| Buprenorphine Formulation | |
|---|---|
| 1 | Buprenex ® |
| 2 | Buprenorphine HCl in 5% Dextrose, pH = 4.7-5.4 |
| 3 | Buprenorphine HCl in 5% Dextrose, pH = 5.4 |
| 4 | Buprenorphine HCl in 5% Dextrose 10% Ethanol 1.8 mg/mL methlyparaben 0.2 mg/mL propylparaben 10 mM Acetate buffer pH = 5.2 |

The results of the study are included in Table 8 below. The results shown below also include the treatment success rates for cats administered the typical low dose of 0.02 mg/kg subcutaneously.

TABLE 8

Success Rate for 24-Hour Treatment with Subcutaneous Buprenorphine

| Group | No. of Study Animals | Surgical Procedure | Formulation | Dose (mg/kg) | Volume (mg/ml) | Frequency (hrs) | Success Rate (percent) |
|---|---|---|---|---|---|---|---|
| 1 | 3 | OHE | 1 | 0.02 | 0.3 | 8 | 33 |
| 2 | 9 | OHE | 2 | 0.06 | 1.2 | 24 | 78 |
| 3 | 9 | OHE | 2 | 0.12 | 1.2 | 24 | 56 |
| 4 | 9 | OHE | 2 | 0.24 | 1.2 | 24 | 100 |
| 5 | 10 | OYN | 3 | 0.24 | 1.2 | 24 | 70 |
| 6 | 6 | OHE | 4 | 0.24 | 2.4 | 24 | 83 |

OHE=Ovariohysterectomy
OYN=Onychectomy

In this study, the dose of 0.24 mg/kg was the most effective (100% [0.24 mg/kg], vs. 33% [0.02 mg/kg], 56% [0.12 mg/kg], and 78% [0.06 mg/kg]). The conventionally used dose of buprenorphine of 0.02 mg/kg administered every eight hours, had a success rate of 33%, and results were included for comparison. Based on the 100% success rate in controlling soft tissue pain, the 0.24 mg/kg dose was evaluated in an orthopedic surgical model (onychectomy) in cats. Success rate in this study was 70%. The success rate was considered acceptable and was not unexpected because onychectomies are more painful than ovariohysterectomies.

A third study was performed because the formulation of the buprenorphine was changed (preservative was added and concentration increased). Efficacy of the new formulation needed to be confirmed. A soft tissue surgery (ovariohysterectomy) was used. Success rate of the dose 0.24 mg/kg was 83%.

As can be seen in Table 8, the higher doses of buprenorphine resulted in higher success rates compared to the traditional low dose of 0.02 mg/kg. These finding are consistent with the ability of a high dose non-extended release buprenorphine formulation to provide prolonged adequate analgesia to a mammal.

Example 3

Safety Studies

The following buprenorphine formulation was tested at various dosages to determine the safety of a high dose non-extended release buprenorphine formulation.

| Component | Amount |
|---|---|
| buprenorphine | 2.4 mg/mL |
| dextrose | 5% |
| methyl paraben | 1.8 mg/mL |
| propyl paraben | 0.2 mg/mL |
| acetate buffer | 10 mM |
| ethanol | 10% |

The pH of the formulation was adjusted to about 4.0.

This study consisted of five treatment groups in which there were four cats (two males, and two females) per treatment group. Treatment groups were designated by dosage. The cats were randomized into one of the treatment groups. The three treatment groups that were administered the test article were Group 1 (5×, 1.2 mg/kg), Group 4 (1×, 0.24 mg/kg), and Group 5 (control). Groups 2 and 3 were not dosed.

The buprenorphine solution was administered by subcutaneous injection for nine consecutive days to three groups of cats (four cats per group). Nine consecutive doses were administered daily to each cat. All doses were administered subcutaneously intrascapularly. At each administration, the cats were observed for pain on injection (e.g. meowing or growling). Body weight from the previous day was used for each dose calculation. Each group of four cats received one of the treatments outlined below in Table 9. For heart rate and respiration rate, each group of cats was evaluated at 30 minutes and at 1, 2, 4, and 7 hours post daily dose.

TABLE 9

Treatment Groups

| Group | Number of Study Animals | Compound | Dose (mg/kg) | Concentration (mg/mL) | Dose Volume (mL/kg) |
|---|---|---|---|---|---|
| 1 | 4 | Buprenorphine Formulation | 1.2 | 2.4 | 0.5 |
| 2* | 4 | Buprenorphine Formulation | 0.72 | 2.4 | 0.3 |
| 3* | 4 | Buprenorphine Formulation | 0.48 | 2.4 | 0.2 |
| 4 | 4 | Buprenorphine Formulation | 0.24 | 2.4 | 0.1 |
| 5 | 4 | Saline | 0 | NA | 0.1 |

*Group 2 and 3 were not dosed.

Reactions to the injections were in different cats at different times during the study, including one control cat treated with saline. All injection site observations were normal during the study. This indicated that the administration of buprenorphine was well-tolerated and did not result in injection site reactions.

No dose of buprenorphine had an effect on body weight over the study period. This was most likely due to the fact that the treatment with buprenorphine did not have an effect on food or water consumption.

The induction of constipation is a concern with opioid administration. In this study, while there was variability in the evidence of defecation, no dose had an effect on the frequency of defecation and all feces notes in the study were normal. Therefore, constipation was not an issue associated with administration of buprenorphine in this study.

Frequency of urination did not appear to be affected by either dose. Additionally, there were no significant findings in the urinalysis, indicating that buprenorphine did not have detrimental effects on the urinary system o the treated cats.

Behavioral side-effects associated with opioid administration are sedation, dysphoria (manic behavior), and euphoria (rubbing, purring, rolling, kneading, etc). Sedation and dysphoria are considered negative behavioral effects, while euphoria is usually considered a positive attribute. Only one cat in the 5× group had evidence of slight sedation and this was only at a single timepoint. The same cat showed signs of dysphoria, several times during the study, which varied in intensity. All groups, including control-treated cats, showed signs of euphoria during the study with no apparent difference between groups. Results indicate buprenorphine has minimal negative effects on behavior and that this only occurred at the 5× dose.

Pupil dilation occurred in both buprenorphine treatment groups but this is a well-known side-effect of all opioids including buprenorphine administered at much lower doses (i.e., 0.02 mg/kg) and is not considered a detrimental side-effect.

Neither dose of the formulated buprenorphine had a clinically relevant effect on clinical pathology parameters. Several cats showed a stress lukogram (leukocytosis with a mature neutrophilia) but this is atypical response for cats that are "stressed" (i.e., being handled during a study). Two different cats showed signs of mild dehydration during the study, but they were limited to one or two timepoints throughout the study. Due to the mild nature and limited duration of dehydration it is not considered clinically relevant. Mild hyperkalemia observed in several cats is suspected to have been an artifact because there were no other hematological abnormalities. The presence of blood and protein in the urine is most likely a result of inflammation induced by repeated cystocentesis. In summary, none of the mild clinical pathology changes are clinically relevant.

Body temperature was within acceptable limits throughout the study in all treatment groups, indicating that formulated buprenorphine did not affect the study cats' ability to thermoregulate.

None of the buprenorphine doses had an effect on heart rate, respiration rate, or mean blood pressure during the study. All heart and lung auscultations were normal.

Therefore, based on these findings, high dose non-extended release buprenorphine formulations are safe, even when administered at five times the dose of 0.24 mg/kg, and for three times as long as the intended duration of administration.

What is claimed is:

1. A method of producing a prolonged analgesic effect in a mammal, the method comprising the step of parenterally administering to a mammal in need of treatment thereof a single high dose of a buprenorphine, wherein said high dose ranges from about 0.12 mg/kg to about 0.3 mg/kg of total mammal body weight, and wherein said dosage provides adequate analgesia to the mammal for a period of at least twelve hours.

2. The method according to claim 1, wherein the mammal comprises canines and felines.

3. The method of claim 1, wherein the buprenorphine is administered by subcutaneous or intramuscular injection as a non-extended release dosage form.

4. The method according to claim 1, wherein the high dose of buprenorphine comprises about 0.24 mg/kg of total mammal body weight of buprenorphine.

5. The method according to claim 1, wherein the high dose buprenorphine provides adequate analgesia to the mammal for a period ranging from 12 hours to about 48 hours.

6. The method according to claim 5, wherein the high dose buprenorphine provides adequate analgesia to the mammal for a period of about 24 hours.

7. The method of claim 6, wherein the buprenorphine is administered once per day, twice per day, every other day, or every two days.

8. The method of claim 6, wherein the parenteral administration comprises subcutaneous administration or intramuscular administration.

9. The method according to claim 6 wherein the high dose of buprenorphine is about 0.24 mg/kg of total mammal body weight.

10. The method according to claim 1 of producing a prolonged analgesic effect in a mammal, wherein said mammal is a feline, the method comprising subcutaneous administering to the feline of a single non-extended release dose of buprenorphine and wherein said dosage provides adequate analgesia to the feline for a period ranging from about 18 hours to about 30 hours.

11. A non-extended release composition for subcutaneous or intramuscular administration to a mammal, the composition comprising: about 0.5 mg/mL to about 3.0 mg/mL buprenorphine or a pharmaceutically acceptable salt thereof, wherein said composition provides a dosage amount of buprenorphine of about 0.12 mg/kg to about 0.24 mg/kg of total body weight; and wherein said composition further comprises about 3% to 5% (v/v) of a tonicity-adjusting agent.

12. The composition of claim 11, wherein the composition comprises about 1.8 mg/mL of buprenorphine or a pharmaceutically acceptable salt thereof.

13. The composition of claim 11, wherein the composition comprises about 2.4 mg/mL of buprenorphine or a pharmaceutically acceptable salt thereof.

14. The composition of claim 11, wherein the tonicity-adjusting agent is dextrose and the composition has a pH range of about 3 to about 5.

15. The composition of claim 11 wherein the composition further comprises from about 0.05 to about 2.5 mg/mL of at least one antimicrobial agent.

16. The composition of claim 11 wherein the composition further comprises from about 5% to about 20% of ethanol.

* * * * *